(12) United States Patent
Deroncelé Thomas et al.

(10) Patent No.: US 11,253,457 B2
(45) Date of Patent: Feb. 22, 2022

(54) EXOPOLYSACCHARIDE-PROTEIN COMPLEX, A METHOD OF PREPARING SAID COMPLEX AND USES THEREOF

(71) Applicant: INSTITUT UNIV. DE CIÈNCIA I TECNOLOGIA, S.A., Mollet del Valles (ES)

(72) Inventors: Victor Manuel Deroncelé Thomas, Mollet del Valles (ES); Rafael Montilla Arevalo, Mollet del Valles (ES); Josep Castells Boliart, Mollet del Valles (ES); Adrián García de la Marina, Mollet del Valles (ES)

(73) Assignee: INSTITUT UNIV. DE CIÈNCIA I TECNOLOGIA, S.A., Mollet del Valles (ES)

( * ) Notice: Subject to any disclaimer, the term of this patent is extended or adjusted under 35 U.S.C. 154(b) by 0 days.

(21) Appl. No.: 16/334,346

(22) PCT Filed: Sep. 19, 2017

(86) PCT No.: PCT/EP2017/073606
§ 371 (c)(1),
(2) Date: Mar. 18, 2019

(87) PCT Pub. No.: WO2019/029833
PCT Pub. Date: Feb. 14, 2019

(65) Prior Publication Data
US 2019/0209452 A1    Jul. 11, 2019

(30) Foreign Application Priority Data
Sep. 19, 2016 (EP) .................................... 16382436

(51) Int. Cl.
| | | |
|---|---|---|
| *A61K 35/74* | (2015.01) | |
| *A61P 35/00* | (2006.01) | |
| *A61K 8/73* | (2006.01) | |
| *A61K 8/99* | (2017.01) | |
| *A61K 47/61* | (2017.01) | |
| *A61Q 19/00* | (2006.01) | |
| *A61K 8/64* | (2006.01) | |
| *A61Q 19/06* | (2006.01) | |
| *A61P 29/00* | (2006.01) | |
| *C12P 19/04* | (2006.01) | |

(52) U.S. Cl.
CPC .................. *A61K 8/73* (2013.01); *A61K 8/64* (2013.01); *A61K 8/99* (2013.01); *A61K 35/74* (2013.01); *A61K 47/61* (2017.08); *A61P 29/00* (2018.01); *A61P 35/00* (2018.01); *A61Q 19/00* (2013.01); *A61Q 19/06* (2013.01); *C12P 19/04* (2013.01)

(58) Field of Classification Search
CPC ........ C07K 14/195-365; C08B 37/006; A61K 31/723; A61K 31/737; A61K 38/164; A61K 47/61; A61K 47/62
See application file for complete search history.

(56) References Cited

U.S. PATENT DOCUMENTS

2015/0079137 A1    3/2015  Delgado-González et al.

FOREIGN PATENT DOCUMENTS

| CN | 104694594 A | 6/2015 |
|---|---|---|
| WO | 2015063240 A1 | 5/2015 |
| WO | 2016067218 A1 | 5/2016 |

OTHER PUBLICATIONS

Quesada, E. et al "Moderately halophilic exopolysaccharide-producing bacteria" Chapter 21 in "Halophilic Microorganisms," Ventosa, A. (ed.), Springer-Verlag, Berlin (Year: 2004).*
Jain, R. et al "Extracellular polysaccharide production . . . " Marine Biotechnol., vol. 7, pp. 184-192. (Year: 2005).*
Courtois, A. et al. "Exopolysaccharides isolated from hydrothermal vent bacteria . . . . " Plos One, vol. 9, iss. 4, pp. 1-7. (Year: 2014).*
Llamas, I. et al "The potential biotechnological applications of the exopolysaccharide . . . " Molecules, vol. 17, pp. 7103-7120. (Year: 2012).*
European Search Report and Written Opinion, dated Feb. 8, 2017 in EP 16382436.0, 5 pages.
Freitas et al., "Advances in bacterial exopolysaccharides: from production to biotechnological applications.", Trends in Biotechnology, 2011, 29(8), 388-398.
International Preliminary Report on Patentability, PCT/EP/2017/073606, Mar. 28, 2019, 7 pages.
International Search Report and Written Opinion, PCT/EP/2017/073606, dated May 14, 2018, 10 pages.
Office Action dated Aug. 25, 2020 in EP 17842382.8, 4 pages.
Office Action dated Aug. 3, 2021 in EP 17842382.8, 2 pages.
Petti, "Detection and Identification of Microorganisms by Gene Amplification and Sequencing", Medical Microbiology, Clinical Infectious Diseases, 2007, 44:1108-1114.

* cited by examiner

*Primary Examiner* — Leigh C Maier
(74) *Attorney, Agent, or Firm* — William R. Childs; Childs Law

(57) ABSTRACT

The present invention relates to an exopolysaccharide-protein complex obtained from a bacterium comprising: (i) a crude exopolysaccharide, and (ii) exopolysaccharide-associated proteins which are derived from outer membrane vesicles and have a molecular weight between 30 and 250 kDa. The present invention further relates to a method for preparing said exopolysaccharide-protein complex and uses thereof.

11 Claims, 5 Drawing Sheets
Specification includes a Sequence Listing.

Figure 5

SEQ ID NO 1.
AACGATCCTAGCTTGCTAGGAGGCGTCGAGCGGCGGACGGGTGAGTAATGCATAGG
AATCTGCCCGGTAGTGGGGGATAACTTGAGGAAACTCAAGCTAATACCGCATACGCC
CTACGGGGGAAAGCAGGGGMTCTTCGGACCTTGCGCTATCGGATGAGCTTATGTCG
GATTAGCTGGTTGGTGAGGTAACGGCTCACCAAGGCGACGATCCGTAGCTGGTCTGA
GAGGATGATCAGCCACATCGGGACTGAGACACGGCCCGAACTCCTACGGGAGGCAG
CAGTGGGGAATATTGGACAATGGGGGCAACCCTGATCCAGCCATGCCGCGTGTGTG
AAGAAGGCCCTCGGGTTGTAAAGCACTTTCAGCGAGGAAGAATGCTTGTCGGTTAAT
ACCCGGCAAGGGAGACATCACTCGCAGAAGAAGCACCGGCTAACTCCGTGCCAGCA
GCCGCGGTAATACGGAGGGTGCGAGCGTTAATCGGAATTACTGGGCGTAAAGCGTG
CGTAGGCGGCTTGATAAGCCGGTTGTGAAAGCCCCGGGCTCAACCTGGGAACGGCA
TCCGGAACTGTTAGGCTAGAGTGCAGGAGAGGAAGGTAGAATTCCCGGTGTAGCGG
TGAAATGCGTAGAGATCGGGAGGAATACCAGTGGCGAAGGCGGCCTTCTGGACTGA
CACTGACGCTGAGGTACGAAAGCGTGGGTAGCAAACAGGATTAGATACCCTGGTAGT
CCACGCCGTAAACGATGTCGACTAGCCGTTGGGGTCCTCGAGACCTTTGTGG

SEQUENCE LISTING

<160> NUMBER OF SEQ ID NOS: 1

<210> SEQ ID NO 1
<211> LENGTH: 784
<212> TYPE: DNA
<213> ORGANISM: Halomonas elongata

```
<400> SEQUENCE: 1
aacgatccta gcttgctagg aggcgtcgag cggcggacgg gtgagtaatg cataggaatc      60
tgcccggtag tgggggataa cttgaggaaa ctcaagctaa taccgcatac gccctacggg     120
ggaaagcagg ggmtcttcgg accttgcgct atcggatgag cttatgtcgg attagctggt     180
tggtgaggta acggctcacc aaggcgacga tccgtagctg gtctgagagg atgatcagcc     240
acatcgggac tgagacacgg cccgaactcc tacgggaggc agcagtgggg aatattggac     300
aatgggggca accctgatcc agccatgccg cgtgtgtgaa gaaggccctc gggttgtaaa     360
gcactttcag cgaggaagaa tgcttgtcgg ttaatacccg gcaagggaga catcactcgc     420
agaagaagca ccggctaact ccgtgccagc agccgcggta atacggaggg tgcgagcgtt     480
aatcggaatt actgggcgta aagcgtgcgt aggcggcttg ataagccggt tgtgaaagcc     540
ccgggctcaa cctgggaacg gcatccggaa ctgttaggct agagtgcagg agaggaaggt     600
agaattcccg gtgtagcggt gaaatgcgta gagatcggga ggaataccag tggcgaaggc     660
ggccttctgg actgacactg acgctgaggt acgaaagcgt gggtagcaaa caggattaga     720
taccctggta gtccacgccg taaacgatgt cgactagccg ttggggtcct cgagaccttt     780
gtgg                                                                  784
```

EXOPOLYSACCHARIDE-PROTEIN COMPLEX, A METHOD OF PREPARING SAID COMPLEX AND USES THEREOF

FIELD OF THE INVENTION

The present invention relates to the field of biotechnology. In particular, the present invention relates to an exopolysaccharide-protein complex obtained from bacteria. The present invention further relates to a method of preparing said complex, a composition comprising thereof and uses thereof.

BACKGROUND OF THE INVENTION

Microbial exopolysaccharides (EPS) are synthesized by a wide variety of bacteria in natural ecological environments, mainly involved in the prevention of desiccation, protection against toxic and/or environmental stresses and adherence to surfaces (De Vuyst, De Vin, Vaningelgem, & Degeest, 2001) (Nwodo, Green, & Okoh, 2012).

The number of EPSs produced by microbial fermentation has gradually increased with many applications in the food and pharmaceutical industries, among others, as their physiological activities differ from those of natural gums and synthetic polymers (Freitas, Alves, & Reis, 2011).

EPS production is among the biochemical strategies used by microorganisms present in hypersaline environments, in order to survive in high saline conditions. Among them, the genus *Halomonas* has received increasing interest as several species are able to produce significant quantities of EPS with high surface activity and/or have rheological properties and applications in food, cosmetic and pharmaceutical sectors (Poli, Anzelmo, & Nicolaus, 2010).

Microbial EPS are biopolymers with a high molecular weight having an extreme diversity in terms of chemical structure and composition. Polysaccharides are the most abundant component of the EPS but previous electron microscopy studies (Nevot, Deroncele, Lopez-Iglesias, et al., 2006; Nevot, Deroncele, Messner, Guinea, & Mercade, 2006), heavily emphasized that other macromolecules such as proteins can also be present.

Along with the general properties such as bio-compatibility, bio-degradability, renewability, flexibility, and eco-friendliness, EPS also offer some important biomedical properties, including antitumor activities (Bazani Cabral de Melo et al., 2015; Ye et al., 2016), antimutagenicity (Miranda et al., 2008), anti-ulcer (Rasulov et al., 1993), anti-inflammatory properties and immune-modulating activities (Ciszek-Lenda, Nowak, Srottek, Gamian, & Marcinkiewicz, 2011).

Anti-inflammatory and immune-modulating activities of EPS are drawing much attention and in lactic acid bacteria were related to the physicochemical properties and structural characteristics of their EPS (Gorska et al., 2014; Shao et al., 2014; Yasuda, Serata, & Sako, 2009). An important mechanism involved in the immunostimulatory activity of polysaccharides is their ability to enhance macrophage function (Beutler, 2004). Polysaccharides were reported to be the active immunomodulators that potentiate both innate and adaptive immunity. They can bind to pattern recognition receptors on the surface of macrophages, such as toll-like receptors, neutrophils, monocytes, NK cells and dendritic cells, and then trigger several signaling pathways to activate macrophages (Kim, Hong, Kim, & Han, 2011). NF-κB, a transcription factor that promote the expression of variety of molecules involved in immune, inflammatory and acute phase responses, including NO and tissue necrosis factor alpha (Li et al., 2015), plays an important role in this activation process.

Recently, a number of studies on the action mechanisms of polysaccharides have demonstrated that polysaccharides could also inhibit the tumor growth in vivo for their immunomodulatory activities (Sun, Li, Qi, Gao, & Lin, 2014; J. Yang, Li, Xue, Wang, & Liu, 2014; Zheng, Wang, & Li, 2015). They exert anti-tumor activity by boosting host's natural immune defense. Other work has suggested that chemopreventive activity of polysaccharides is based on their tumor anti-initiating activity through their modulation of carcinogen metabolism, in addition to the tumor anti-promoting activity through their anti-inflammatory activity (Gamal-Eldeen, Ahmed, & Abo-Zeid, 2009; Raafat, Gamal-Eldeen, El-Hussieny, Ahmed, & Eissa, 2014).

Document WO2015063240A1 describes the cosmetic and/or dermopharmaceutical use of an EPS produced by *Halomonas anticariensis*, specifically, for the treatment and/or care of the skin, and in particular, its use for inflammation, lipolysis, lipid accumulation and skin firmness. However, this document does not disclose the combination of extracellular polysaccharides and selected associated-proteins and its use.

Document WO 2015/117985 relates to a strain of *Pseudomonas*, a cold-adapted bacteria, useful for cosmetic compositions. However, this document does not encompass the use of the crude exopolymeric material, including the associated protein. The composition discloses the use of a partial or completely hydrolized EPS derived from *Pseudomonas* for several purposes, including dermoprotection.

Document WO 2010/023178 A1 describes the use of bacterial polysaccharide derived from species of the genera *Bifidobacterium, Streptococcus* and *Lactobacillus*, some of which are considered as probiotic bacteria for treating inflammatory diseases, specifically, colitis or Crohn's disease. The application evaluated the anti-inflammatory potential of the purified EPS in a murine dendritic cell assay and/or an assay involving a human intestinal epithelial cell line. However, this document does not disclose the combination of extracellular polysaccharides and selected associated-proteins and its use.

U.S. Pat. No. 7,348,420 B2 describes the recombinant expression of cell wall, cell surface, and secreted proteins of *Lactobacillus acidophilus* potentially useful for the treatment or prevention of cancer, particularly colon cancer. However, this document does not disclose the combination of extracellular polysaccharides and selected associated-proteins and its use.

U.S. Pat. No. 8,129,518 B2 provided synthetic polysaccharide antigens with anti-inflammatory or inflammatory immunomodulatory properties. However, this document does not disclose the combination of extracellular polysaccharides and selected associated-proteins and its use. In this case the synthetic polysaccharide is composed mainly of lipopolysaccharide, and bacterial cell wall glycopeptides, also known as murein or peptidoglycan, from both Gram negative and Gram positive bacteria.

U.S. Pat. No. 8,088,605 B2 discloses a delivery system for active molecule comprising exopolysaccharide micelles produced by a *Lactobacillus* strain. These includes active molecules such as DNA, RNA, protein, peptide, peptidomimetic, virus, bacteria, nutraceutical product and pharmaceutical agent with analgesic, anesthetic, antibiotic, anticancer, anti-inflammatory, and antiviral properties. However, these pharmaceutical agents are not produced by the bacterium.

WO 2009/127057 A1 discloses a skin care composition comprising one exopolysaccharide derived from a microbial mat. This document discusses the use of different compositions for cosmetic or therapeutic approaches and provides examples for evaluating the effects of the EPSs on the synthesis of hyaluronic acid, lipid synthesis, among others, related with cosmeceuticals applications. However, this document does not disclose the combination of extracellular polysaccharides and selected associated-proteins and its use as anti-inflammatory or immunomodulatory agents.

CN 104694594 discloses a preparation method of a sea cucumber epiphytic *Bacillus subtilis* exopolysaccharide that can be used in the anti-tumor medicines, cosmetic additives and other fields. The principal application exposed in this document is related with the application of this EPS in bacterial and plant pathogen growth inhibition, a peroxide scavenger, anti-tumor and inhibition of microapplication.

U.S. Pat. No. 9,095,733 discloses methods of using polysaccharides for applications in topical personal care products, cosmetics, and for wrinkle reduction compositions. Particularly, this document provides compositions of microalgal cells with high value cosmeceutical ingredients such as carotenoids, polyunsaturated fatty acids, moisturizing polysaccharides, superoxide dismutase, and other components. However, this document does not disclose the combination of extracellular polysaccharides and selected associated-proteins and its use as anti-inflammatory or immunomodulatory agents.

WO 2013/082915 A1 discloses a strain of exopolysaccharide-secreting *Lactobacillus brevis*, and its applications in medicaments, healthcare products and food products for immunity enhancement. The exopolysaccharide extract is obtained after precipitating protein via trichloroacetic acid method to remove the protein.

Filomena Freitas et al. "Advances in bacterial exopolysaccharides: from production to biotechnological applications", Trends In Biotechnology, vol. 29, no. 8, 2011, discloses EPSs composed of carbohydrates like glucose, galactose, mannose, rhamnose and fucose which in the purification process may contain impurities of proteins.

Anthony Courtois et al. "Exopolysaccharides isolated from hydrothermal vent bacteria can modulate the complement system", Plos One, vol. 9, No. 4, 2014, disclose EPSs from *Alteromonas infernus* wherein the proteins are also considered as impurities since no biological function/activity is determined.

WO 2016/067218 discloses EPSs of *Halomonas eurhalina* containing rhamnose, galactose, glucose, D-glucosamine and glucouronic acid with low molecular weight proteins (10 kDa), being higher molecular weight proteins removed from the polymer.

It is well known that the protein content detected in the EPS are released to the media through membrane vesicles. Gram-negative bacteria constitutively secrete native outer membrane vesicles (OMVs) into the extracellular milieu, and recent progress in this area has revealed that OMVs are essential for bacterial survival.

The protein composition of these exopolimeric matrix has been studied to a considerably lesser degree than its polysaccharide composition, although protein content in some biopolymers may exceed their polysaccharide content. The production of these proteins inside of OMVs is one of the general envelope stress responses. Various stress factors such as temperature, nutrient depletion and exposure to harmful chemical agents may induce accumulation and aggregation of misfolded proteins in the periplasm. Packaging of these stress-products into OMV and their releases represents an efficient mechanism of alleviating stress.

The present invention intends to preserve the entire composition of the exopolimeric material, i.e., the capsular polysaccharide with the OMVs, in order to use the proteins contained thereof. Accordingly, the present invention makes use of low-speed centrifugations, and differential filtration steps to remove residual bacteria and preserve the proteins inside the polymer, i.e as an exopolysaccharidic complex, decorated with membrane vesicles, in which proteins are concentrated in order to reduce adverse conditions generated by certain factors, such as ultraviolet radiation, oxidative stress, hypersalinity, among others.

Thus, the above prior art known processes relating to the production of EPS from microbial sources do not disclose the combined effect of polysaccharide fraction with selected extracellular EPS-associated proteins which are derived from outer membrane vesicles and have a molecular weight between 30 and 250 kDa.

The present inventors have surprisingly found that an exopolysaccharide-protein complex secreted by bacteria exhibits unique immunomodulating properties, is non-cytotoxic and non-proliferating to normal cell lines. The exopolysaccharide-protein complex ameliorates pro-inflammatory chemokines expression and induces the production of other anti-inflammatory cytokines of cells in culture. It has the activity of inhibiting growth of tumor cell lines. These properties have been found to be enhanced when the crude exopolymer are associated with the proteins derived from outer membrane vesicles.

Accordingly, the complex can be used for treatment or prevention of diseases in which inflammation and immunomodulation are critical or as adjuvant in medical treatment, such as those related to an imbalance of the production of anti-inflammatory or proinflammatory cytokines, and also for preparing anti-tumor drugs.

BRIEF DESCRIPTION OF THE DRAWINGS

FIG. 5 shows the partial 16S rRNA gene sequence of the isolate according to example 1.

SUMMARY OF THE INVENTION

Figure 1:
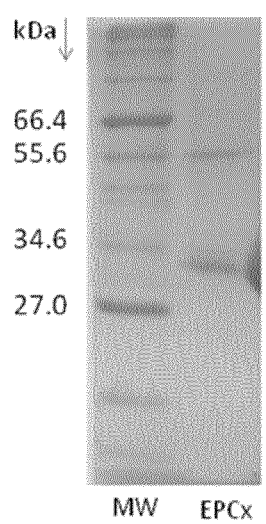
FIG. 1 shows sodium dodecyl sulfate polyacrylamide gel electrophoresis (SDS-PAGE) gel of EPCx. Analysis from SDS-PAGE gel indicates that the two principal bands have molecular weights of ~33 kDa and ~55 kDa, respectively.

A first object of the invention relates to an exopolysaccharide-protein complex obtained from a bacterium comprising: (i) a crude exopolysaccharide, and (ii) exopolysaccharide-associated proteins which are derived from outer membrane vesicles and have a molecular weight between 30 and 250 kDa.

A second object of the invention relates to a method of preparing an exopolysaccharide-protein complex according to the first object.

A third object of the invention relates to a composition (pharmaceutical, nutraceutical or cosmeceutical) comprising an exopolysaccharide-protein complex according to the first object.

A fourth object of the invention relates to the use of the composition according to the third object of the invention and the exopolysaccharide-protein complex according to the first object of the invention.

DETAILED DESCRIPTION OF THE INVENTION

Definitions

In order to facilitate the comprehension of this invention, the meanings of some terms and expressions as used in the context of the invention are included.

As used herein, the term "isolated" should be considered to mean material removed from its original environment in which it naturally occurs, for example, a bacterial strain from hypersaline environment.

As used herein, the term "EPS" or "exopolysaccharide" or "EPSx" should be understood to mean high molecular weight polymers that are composed of sugar residues and expressed by bacteria.

As used herein, "activation of NF-κB (nuclear factor-kappa B)" means the process by which stimulation of NF-κB mediated by Toll-like receptors activates NF-κB, subsequently facilitating increased transcription of mRNA coding for intracellular production of particular chemokines and cytokines and subsequent translation of the transcribed mRNA, resulting in increased amounts of particular cytokines and chemokines that are both present intracellularly and released by the eukaryotic cell into the intercellular environment.

As used herein, "interleukin" means any of a group of cytokines (secreted signaling molecules) that were first seen to be expressed by white blood cells. Interleukins are commonly designated using an abbreviation: e.g. IL-6, IL-8, etc.

As used herein, the term "immunomodulatory" refers to its ability to modulate the response of cells of the human immune system.

As used herein, "anti-inflammatory" refers to the ability to induce the production of interleukin-10, a potent anti-inflammatory cytokine and to block the production of interleukin 12, a cytokine pro-inflammatory nature.

As used herein, "cancer" and "tumor" refer to or describe the physiological condition in mammals that is typically characterized by unregulated cell growth.

As used herein, the term "anticancer activity" as used herein refers to preferential cytotoxic effect against tumor cells without any significant adverse effects to normal cells under the same conditions of exposure.

As used herein, the term "nutraceutical" refers to any compounds or chemicals that can provide dietary or health benefits when consumed by humans or animals.

As used herein, the term "cosmeceutical composition" refers to a composition that is employed as both a cosmetic composition and as a pharmaceutical composition.

As used herein, the term "adjuvant" refers to an embodiment of the invention provided to a subject in conjunction with a medical treatment plan.

As used herein, "immunomodulation", "immunomodulatory", and similar terms refer to the ability to modify the immune responses in a subject in a way that may have healthful benefits, such as to produce an anti-inflammatory or an immunostimulatory effect.

As used herein, "RT-PCR" means reverse transcription polymerase chain reaction (RT-PCR), a laboratory technique for amplifying a defined piece of a ribonucleic acid (RNA) molecule. The RNA strand is first reverse transcribed into its DNA complement or complementary DNA, followed by amplification of the resulting DNA using polymerase chain reaction. This can either be a 1 or 2 step process.

As used herein, the term "exopolysaccharide-protein complex" should be understood as an entity in which the proteins are not found as mere impurities. In contrast, they contribute to the biological effect/activity of the complex which is different from that obtained for the exopolysaccharide alone.

As used herein "preventing or treating" does not exclude that both actions "preventing" and "treating" can be carried out on the same subject.

EMBODIMENTS

In a first aspect the present invention relates to an exopolysaccharide-protein complex (also called herein EPCx) obtained from a bacterium, preferably wherein said bacterium is from a genus selected from *Halomonas*, *Pseudoalteromonas*, *Vibrio*, *Salinivibrio*, *Marinomonas*, *Alteromonas*, *Pseudomonas*, *Halobacillus*, and *Bacillus*, more preferably from genus *Halomonas*, still more preferably from *Halomonas elongata* sp., comprising: (i) a crude exopolysaccharide, and (ii) exopolysaccharide-associated proteins which are derived from outer membrane vesicles and have a molecular weight between 30 and 250 kDa. In this context, the term "comprising" should be understood as the components of the exopolysaccharide-protein complex are not limited to (i) a crude exopolysaccharide, and (ii) exopolysaccharide-associated proteins which are derived from outer membrane vesicles and have a molecular weight between 30 and 250 kDa.

In another embodiment, said exopolysaccharide-protein complex obtained from a bacterium consists of: (i) a crude exopolysaccharide, and (ii) exopolysaccharide-associated proteins which are derived from outer membrane vesicles and have a molecular weight between 30 and 250 kDa. In this context, the term "consists of" should be understood as the components of the exopolysaccharide-protein complex are exclusively (i) a crude exopolysaccharide, and (ii) exopolysaccharide-associated proteins which are derived from outer membrane vesicles and have a molecular weight between 30 and 250 kDa.

In a preferred embodiment, the exopolysaccharide-protein complex of the present invention relates to an exopolysaccharide-protein complex comprising: (i) a crude exopolysaccharide, and (ii) exopolysaccharide-associated proteins which are derived from outer membrane vesicles and have a molecular weight between 30 and 250 kDa, wherein the crude exopolysaccharide is a heteropolymer comprising or consisting of:
  glucose units;
  galactose units;
  uronic acid units; and
  other sugar units selected from rhamnose, glucosamine and a mixture of rhamnose and glucosamine.

In a further preferred embodiment, the exopolysaccharide-protein complex of the invention comprises or consists of:
(a) 30 to 60 wt % glucose;
(b) 30 to 50 wt % galactose;
(c) 5 to 10 wt % uronic acids; and
(d) 1 to 10 wt % of other sugar units,
providing that the sum of the components of the crude exopolysaccharide is 100 wt %, i.e. the components (a), (b), (c) and (d) must amount 100 wt % if components (a), (b), (c)

and (d) are the only components in the exopolysaccharide-protein complex or the components (a), (b), (c) and (d) plus any further component(s) must amount 100 wt % if components (a), (b), (c) and (d) are not the only components in the exopolysaccharide-protein complex.

In a further preferred embodiment, in the exopolysaccharide-protein complex, the crude exopolysaccharide further comprises sulfate, preferably at a concentration from 2 to 10 wt %.

In a further preferred embodiment, in the exopolysaccharide-protein complex, the exopolysaccharide-associated proteins which are derived from outer membrane vesicles and have a molecular weight between 30 and 250 kDa include two bands of molecular weight as obtained by SDS-PAGE. In particular, the EPCx has a protein profile comprising at least, according to the SDS-PAGE technique, 12 detectable bands, including two principal bands, corresponding, respectively, to molecular weights (approximate molecular weights given in relation to molecular standards, notably provided by Bio-Rad Laboratories) ranging between:

band 1: 30 kDa and 40 kDa, in particular 33 kDa;
band 2: 51 kDa and 60 kDa, in particular 55 kDa.

In a second aspect, the present invention relates to a method of preparing an exopolysaccharide-protein complex according to the first aspect of the invention, including each of the embodiments comprised in said first aspect and combinations thereof.

The method of preparing an exopolysaccharide-protein complex comprises the steps of:
culturing one or more bacteria from genus including, but not limited thereto, *Halomonas, Pseudoalteromonas, Vibrio, Salinivibrio, Marinomonas, Alteromonas, Pseudomonas, Halobacillus, Bacillus* or any other bacterium isolated from a hypersaline environment, the term "hypersaline" referred to a kind of extreme environments that have salt concentrations much greater than that of seawater, often close to or exceeding salt saturation;
isolating the exopolysaccharide-protein complex from the secreted fraction of the culture.

In a preferred embodiment, the genus is selected from *Halomonas, Pseudoalteromonas, Vibrio, Salinivibrio, Marinomonas, Alteromonas, Pseudomonas, Halobacillus,* and *Bacillus*. In a more preferred embodiment, said bacteria genus is *Halomonas* and in a more preferred embodiment, *Halomonas elongata* sp. is used as a bacterium belonging to *Halomonas* genus.

The medium suitable to cultivate the above mentioned bacteria includes a synthetic medium comprising a carbon source selected from the group consisting of: lactose, maltose, glucose, galactose, sucrose, glycerol and mixtures thereof. Preferably, the carbon source is selected from the group consisting of: glucose, lactose, sucrose, and mixtures thereof. In a more preferred embodiment, the carbon source is lactose.

In a particular embodiment, the other fermentation medium components are: potassium phosphate dibasic ($K_2HPO_4$), 0.5-1.0 wt %; potassium phosphate monobasic ($KH_2PO_4$), 0.1-0.5 wt %; sodium chloride (NaCl), 5.0-10.0 wt %; magnesium sulfate heptahydrate ($MgSO_4 \cdot 7H_2O$), 0.01-0.05 wt %; ammonium sulfate $(NH_4)_2SO_4$, 0.05 wt %-0.5 wt % and peptone, 0.02-0.1 wt %.

In a preferred embodiment, before culturing bacteria, the suitable medium for culturing is a synthetic medium with a pH value ranging from 6 to 8. In a more preferred embodiment, the suitable medium has a pH value of 7.

In another preferred embodiment, the culture step is conducted in fermenters operating at a temperature ranging from 25° C. to 37° C. In a more preferred embodiment, the temperature is 32° C.

In a particular embodiment, the present invention provides a fermentation process comprising a fermentation step allowing to grow a strain of the corresponding bacteria, preferably wherein said bacteria is from a genus selected from *Halomonas, Pseudoalteromonas, Vibrio, Salinivibrio, Marinomonas, Alteromonas, Pseudomonas, Halobacillus,* and *Bacillus*, more preferably from genus *Halomonas*, still more preferably from *Halomonas elongata* sp., in a suitable medium in a fermenter under conditions of agitation sufficient to maintain a homogenous culture and limited aeration such that dissolved oxygen pressure (pO2) within the culture is around 20 to 40% for most of the fermentation step. Preferably, pO2 within the culture is 30% in the fermentation step.

As mentioned above, the inventive process of preparing an exopolysaccharide-protein complex comprises the step of isolating the exopolysaccharide-protein complex from the secreted fraction of the culture. Said isolation can be carried by removing other molecules present in the culture media by alcohol precipitation. Non-limiting examples of alcohols which can be used include ethanol, isopropanol, and methanol. In particular, the isolation and purification of the EPCx after alcohol precipitation can be conducted by tangential flow filtration methods using ultrafiltration membranes. Preferably, said membranes have a MWCO of 30 kDa and the retentate recovered after the ultrafiltration comprises the exopolysaccharide and the EPS-associate proteins which can be recovered. The tangential flow filtration can act to both diafilter and concentrate the EPCx.

In a third aspect, the present invention relates to a composition (pharmaceutical, nutraceutical or cosmeceutical) comprising an exopolysaccharide-protein complex according to the first object of the invention, including each of the embodiments comprised in said first aspect and combinations thereof.

In a preferred embodiment, said composition further comprises a biological response modifier selected from the group consisting of lymphokine, interleukin, growth factor and NFkB factor.

In a fourth aspect, the present invention relates to a composition comprising an exopolysaccharide-protein complex according to the first object of the invention, including each of the embodiments comprised in said first aspect and combinations thereof, for use in stimulating an immune response in a subject for preventing or treating a disease selected from cancer or a disease associated to undesirable inflammatory activity.

Accordingly, the present invention also relates to a method for preventing or treating a disease selected from cancer or a disease associated to undesirable inflammatory activity, the method comprising administering to a subject in need thereof a therapeutically effective amount of an exopolysaccharide-protein complex according to the first object of the invention, including each of the embodiments comprised in said first aspect and combinations thereof, or a composition comprising thereof.

In a preferred embodiment, said disease associated to undesirable inflammatory activity is selected from allergy, Alzheimer's disease, arthritis, autoimmune deficiency syndrome, celiac disease, diabetes mellitus, gastrointestinal disorder, inflammatory bowel disease, interstitial cystitis, skin disorders, acne, arteritis, arthritis, cancer, cellulitis, dermatitis and cardiovascular diseases.

In another preferred embodiment, said cancer is liver cancer or a hepatocellular carcinoma.

In another preferred embodiment, said exopolysaccharide-protein complex according to the first object of the invention, including each of the embodiments comprised in said first aspect and combinations thereof, is used as an anticancer agent or adjuvant agent for cancer therapies.

In another embodiment, the present invention provides an in vitro toxicity test to evaluate the cytotoxic potential of EPCx on non-tumor cell lines. The cytotoxicity evaluation of each concentration of EPCx was performed by using the MTT Cell Proliferation Assay in order to determine the concentrations which are not harmful to Human Epidermal Keratinocytes (HEK) and human monocyte-like cells (THP-1).

As shown in the example section, the EPCx show in vitro anti-proliferative activity against a panel of one or more cancer cell lines, including human lung adenocarcinoma cell line (H1975), Human melanoma cell line (A375), and human hepatocellular carcinoma cell line (HepG2). The anticancer properties of EPCx was ascertained by MTT assay and showed that EPCx significantly inhibit the growth of human lung adenocarcinoma cell line (H1975), Human melanoma cell line (A375), and human hepatocellular carcinoma cell line (HepG2).

The immunomodulatory and anti-proliferative properties of EPCx were ascertained by the analysis of the induced activation of human primary keratinocytes (HEK) and human monocyte-like cells (THP-1) stressed with LPS (lipopolysaccharide), analyzing the expression of mRNA for the cytokines IL-6, IL-8, IL-10 and TNF-α by real-time PCR and the NF-κB activation using a luciferase reporter gene assay.

The immunomodulatory and anti-cancer properties of the EPCx, are showed preferably at EPCx concentrations between 0.01 mg/ml to 1.0 mg/ml.

Accordingly, the inventors have surprisingly and unexpectedly found that an EPCx obtained from a bacterium, preferably wherein said bacterium is from a genus selected from *Halomonas, Pseudoalteromonas, Vibrio, Salinivibrio, Marinomonas, Alteromonas, Pseudomonas, Halobacillus*, and *Bacillus*, more preferably from genus *Halomonas*, still more preferably from *Halomonas elongata* sp., in accordance with the invention, can be used as anti-inflammatory and/or immunomodulator agent, and is in particular able to inhibit a pro-inflammatory stimulation of normal cells in culture. In addition EPCx exhibits tumor anti-promoting properties in cancer cell lines culture.

The present invention will be more clearly understood with the help of the following examples, without being the present invention limited thereto and included only for illustrative purposes only, showing isolation and characterization of bacteria, the preparation and characterization of EPCx and assays for biological activities in accordance with the invention.

EXAMPLES

Example 1: Isolation and Identification of the Microorganism

Isolation of the Microorganism.

A microorganism included in the present invention (deposited with number DSM 32408 at the depositary institution Leibniz-Institut DSMZ-Deutsche Sammlung von Mikroorganismen und Zellkulturen GmbH by INKEMIA IUCT (Institut Univ. de Ciència i Tecnologia) Group) is isolated from a rock salt from solar salternsin Cardona (Spain) by serial dilution and plating on MH agar medium (Ventosa, Garcia, Kamekura, Onishi, & Ruizberraquero, 1989). The plates were incubated at 32° C. for 3 to 5 days, and bacterial colonies were isolated in pure form and maintained on slopes of the same medium.

To evaluate the EPS production capability, the bacterium isolates was grown in MY medium (Moraine & Rogovin, 1966) supplemented with 5-10% NaCl for 3-5 days at 32° C. under continuous shaking (120 rpm). The EPS from the growing culture was isolated using the method as described by Quesada et al. (Quesada, Bejar, & Calvo, 1993) and used for quantification and chemical analysis.

Identification of the Microorganism

The selected microorganism was analyzed by physiological and biochemical methods following standard microbiological methods (Table 1). As a result, based on physiological and biochemical analysis thereof, the microorganism of the present invention was confirmed to have similarity to *Halomonas* genus.

TABLE 1

Morphological and physiological characteristics of the isolated microorganism.
Character

| Morphological characters | |
|---|---|
| Colony morphology | Cream, circular |
| Gram nature | − |
| Cell shape | Rod |
| Cell arrangement | Single |
| Motility | + |
| Pigmentation | − |
| Physiological characters | − |
| pH range for growth | 5-11 |
| pH optimum for growth | 8 |
| Temp. range for growth (° C.) | 22-40 |
| Temp. optimum for growth (° C. | 32 |
| NaCl range for growth (%) | 1-20 |
| NaCl optimum for growth (%) | 5 |
| Growth on King's B medium | + |
| Growth on McConky agar | − |
| Biochemical characters | |
| Voges-Proskauer test | − |
| Citrate utilization | + |
| Methyl red test | − |
| Production of | |
| Gelatinase | − |
| Urease | − |
| Catalase | + |
| Nitrate reductase | + |
| H2S | − |
| Lysine decarboxylase | − |
| Arginine decarboxylase | − |
| Ornithine decarboxylase | − |
| Indole | − |
| Phenylalanine deaminase | + |
| Tryptophan deaminase | − |
| Tentative identity | Halomonas |

In order to identify more precisely, the present inventors analyzed base sequence of ribosome small subunit gene. Particularly, genomic DNA was separated by using MasterPure™ DNA purification from Epicentre® Biotechnologies Germany according to the manufacturer's instruction. PCR mediated amplification of 16S rDNA and purification of the PCR product was carried out as described previously (Rainey, WardRainey, Kroppenstedt, & Stackebrandt, 1996). As a result of database analysis on the decided base sequence using NCBI (National Center for Biological Information) BLAST, the microorganism was confirmed to have similarity to *Halomonas* genera. However, it had a little difference from the typical *Halomonas elongata*, so that the microorganism of the present invention was finally named as *Halomonas elongata*.

Partial sequencing of the 16S rRNA gene (844 bp) indicated that the strain belongs to the species *Halomonas elongata*. The partial 16S rRNA gene sequence is shown in FIG. 5.

Example 2. Preparation and Isolation of the Exopolysaccharide-Protein Complex (EPCx) Excreted by *Halomonas* Elongate According to Example 1 a) Method of Culturing of Strain the Species *Halomonas elongata*

The strain of the species *Halomonas elongata* (deposited with number DSM 32408 at the depositary institution Leibniz-Institut DSMZ-Deutsche Sammlung von Mikroorganismen and Zellkulturen GmbH by INKEMIA IUCT (Institut Univ. de Ciència i Tecnologia) Group) was cultured in a fermenter, at 32° C. and at a pH of 7.5, whose broth contained (g $L^{-1}$): 100 NaCl; 50 Lactose; 7 $K_2HPO_4$; 2 $KH_2PO_4$; 0.1 $MgSO_4.7H_2O$; 1 $(NH_4)_2SO_4$ and 0.5 Peptone. An inoculum was prepared with 10% (v/v) of a pre-culture and the duration of the fermentation was extended to 72 hours. The reactors are operated in batch mode, and dissolved oxygen was controlled by the agitation (300 to 900 rpm) at $pO_2 \approx 30\%$.

b) Purification of EPCx

The bacteria were separated from the broth by centrifugation at 12,000 g for 45 min. The resulting clear solution was subjected to ultrafiltration and dialysis using an installation for ultrafiltration (Sartocon® Slice Cassette, Sartorius Stedim), membrane exclusion limit 30 KDa. If necessary, the final solution may be lyophilized and purified obtaining an exopolysaccharide-protein complex with a yield of 60-80%.

Example 3. Physical-Chemical Characterization of EPCx Produced by *Halomonas* Elongate The content of neutral and acid monosaccharides of the exopolysaccharide obtained according to Example 2 was determined by a method described by Honda et al. (Honda et al., 1989) and Yang et al. (X. B. Yang, Zhao, Wang, Wang, & Mei, 2005; X. B. Yang, Zhao, Zhou, et al., 2005). Briefly, the purified polysaccharide sample (1 mg) was hydrolyzed with 1 ml of 2 M trifluoroacetic acid at 120° C. for 2 h, derivatized with 1-phenyl-3-methyl-5-pyrazolone, and subsequently analyzed by high-performance liquid chromatography with detection by absorbance monitoring at 245 nm.

The percent relationship of sugars obtained was 30-60% of glucose, 30-50% galactose, 5-10% of glucuronic acid, 1-10% of rhamnose and 1-10% of glucosamine, being the amounts consistent with a total of 100%.

Sodium dodecyl sulfate-polyacrylamide gel electrophoresis (SDS-PAGE) (Laemmli, 1970) was carried out with a 4% stacking and a 9% separating gel. The EPCx sample was dissolved at 10 mg/mL in distilled water and added at 1:3 volume ratio into a buffer solution of 0.5% SDS with 1%-mercaptoethanol, and then heated to boiling for 5 min. The gels were stained with Coomassie Brilliant Blue R-250 to visualize proteins. 12 detectable bands, including three principal bands of 38 kDa, 46 kDa and 54 kDa were observed (see FIG. 1).

Example 4. Effect of Exopolysaccharide-Protein Complex on Non-Tumor Cell Lines (Viability In Vitro)

The cytotoxicity evaluation of exopolysaccharide-protein complex was performed by using the MTT assay in order to determine the concentrations which are not harmful to Human Epidermal Keratinocytes (HEK) and human monocyte-like cells (THP-1). Proliferation of cells lines was measured based on the mitochondria-dependent reduction of yellow tetrazolium MTT (3-(4, 5-dimethylthiazolyl-2)-2, 5-diphenyltetrazolium bromide), to generate reducing equivalents such as NADH and NADPH. Briefly, $5 \times 10^3$ cells in 100 μL per well were plated in 96-well tissue culture plates for 24 h. Cells were incubated for 72 h in the presence of different concentrations of EPS (1, 0.1 and 0.01 mg/ml). After that, 20 μL of MTT solution (5 mg/mL in PBS) were added into each well and followed by further incubation for 4-5 h. The resulting intracellular purple formazan can be solubilised and quantified by spectrophotometric means. The results are given in Table 2 below.

TABLE 2

Effect of exopolysaccharide-protein complex non-tumor cell lines.

| Cell line | Concentration (mg/ml) | Cell viability % of MTT conversion |
|---|---|---|
| HEK | 1 | 101 |
|  | 0.1 | 98 |
|  | 0.01 | 102 |
| THP-1 | 1 | 102 |
|  | 0.1 | 97 |
|  | 0.01 | 104 |

No viability alteration and no significant changes in cells proliferation were observed at the exopolysaccharide-protein complex concentrations tested in this assay on normal cell lines (table 2).

Example 5. Effects of Exopolysaccharide-Protein Complex in HEK and THP-1 Cells Stressed with LPS The capacity of EPS to modulate the inflammatory response was evaluated in vitro in human primary keratinocytes (HEK) and human monocyte-like cells (THP-1) stressed with LPS (lipopolysaccharide). The cells were pretreated with different concentrations of exopolysaccharide-protein complex (1, 0.1 and 0.01 mg/ml) for 24 h and with 10 μg/ml of LPS for 24 h. Controls of HEK and THP-1 cells treated only with the different concentrations of exopolysaccharide-protein complex (1.0, 0.1 and 0.01 mg/ml) were also prepared.

Expression of mRNA for the cytokines IL-6, IL-8, IL-10 and TNF-α was analyzed by real-time PCR and the NF-κB activation was measured using a luciferase reporter gene assay.

Real-time PCR: Total RNA was extracted with the RNA Isolation Kit (ThermoFischer Scientific) according to the manufacturer's recommendations. 1 ng of RNA was reverse transcribed into complementary DNA (cDNA) using Superscript One-Step RT-PCR kit with platinum Taq according to the instructions (Invitrogen). Quantification rests on the measure of threshold cycles (CT), which are measured at the beginning of the exponential phase of the reaction and on the normalization of the internal standard curve obtained with the reference gene.

When HEK and THP-1 cells were pretreated with exopolysaccharide-protein complex (EPCx) before stimulation with LPS, we did not observe the upregulation of pro-inflammatory cytokines (IL-6, IL-8, and TNF-α), as occurred in the LPS-treated cells. However, cells pretreated with EPCx before stimulation with LPS shows a downregulation of anti-inflammatory cytokine, IL-10 (tables 3 and 4).

TABLE 3

Gene expression (mRNA, real-time PCR) of pro-inflammatory cytokines (IL-6, IL-8, and TNF-α) and anti-inflammatory cytokine (IL-10) in keratinocytes stresses with LPS and treated with different concentrations of EPCx (1.0, 0.1 and 0.01 mg/ml).
Gene expression (mRNA, real-time PCR)

|  | IL-6 | IL-8 | TNF-α | IL-10 |
|---|---|---|---|---|
| Control | 3 | 2 | 4 | 1 |
| LPS | 62 | 59 | 67 | 7 |
| EPCx 0.01 | 12 | 17 | 21 | 11 |
| EPCx 0.1 | 17 | 14 | 27 | 18 |
| EPCx 1.0 | 15 | 18 | 31 | 22 |

TABLE 4

Gene expression (mRNA, real-time PCR) of pro-inflammatory cytokines (IL-6, IL-8, and TNF-α) and anti-inflammatory cytokine (IL-10) in human monocyte-like cells stresses with LPS and treated with different concentrations of EPCx (1,0.1 and 0.01 mg/ml).
Gene expression (mRNA, real-time PCR)

|  | IL-6 | IL-8 | TNF-α | IL-10 |
|---|---|---|---|---|
| Control | 1.5 | 3 | 2 | 1 |
| LPS | 73 | 82 | 67 | 5 |
| EPCx 0.01 | 21 | 27 | 32 | 12 |
| EPCx 0.1 | 27 | 30 | 44 | 12 |
| EPCx 1.0 | 15 | 18 | 31 | 15 |

Measurement of NF-κB activation: NF-κB activation was measured using a luciferase reporter gene assay. For this assay THP-1 macrophages ($1 \times 10^5$ cells well$^{-1}$) were transfected with the pNF-κBluciferase reporter gene construct (Stratagene) using Lipofectamine LTX plus (Invitrogen). Sixteen hours after transfection, different concentrations of EPS (1, 0.1 and 0.01 mg/ml) were added and the incubation was continued for a further 8 h. The cells were then washed with NaCl/P; and lysed using lysis buffer (200 μL·well$^{-1}$) (25 mM glycylglycine, 15 mM MgSO$_4$, 4 mM EGTA, 1 mM dithiothreitol and 1% Triton X-100). Lysed cells were centrifuged (5 min, 9000 g) and stored at −80° C. until assay. Luciferase activity was measured using luciferin (1 mM in glycylglycine buffer, 300 μL·sample$^{-1}$) in a luminometer at 562 nm.

Figure 2:
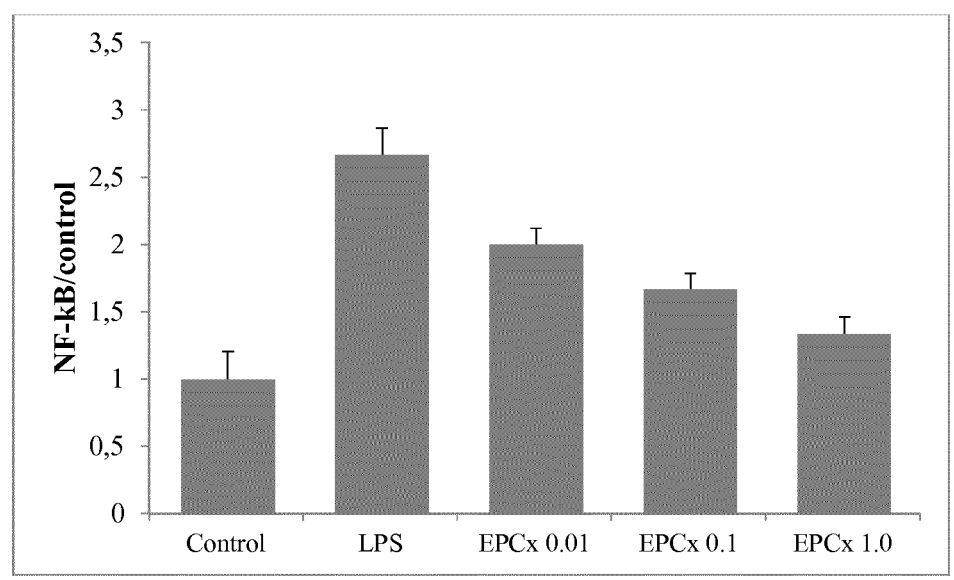
FIG. 2 shows the effect of EPCx on NFκB activation in LPS-stimulated keratinocytes.
Figure 3:
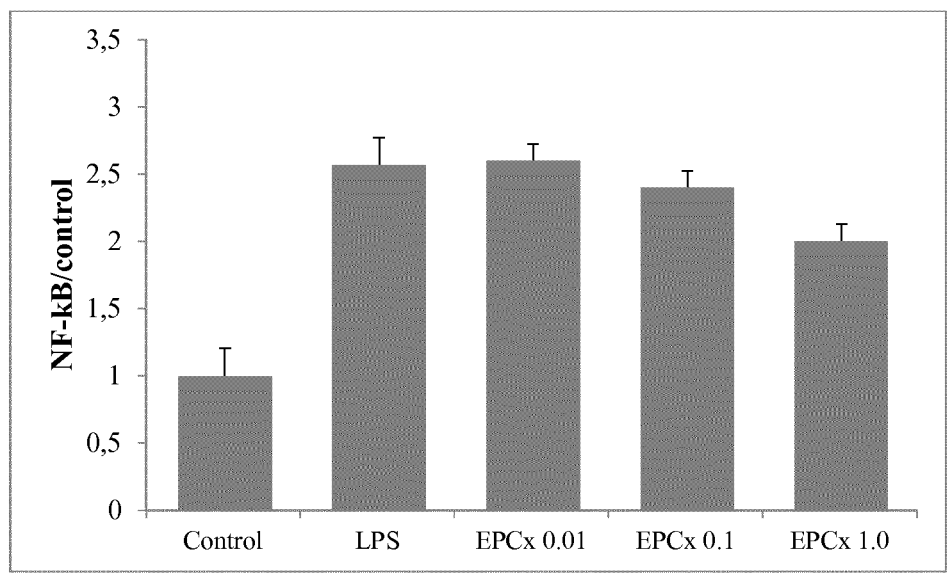
FIG. 3 shows the effect of EPCx on NFκB activation in LPS-stimulated THP-1 cells.

EPCx dose-dependently downregulated the NF-κB transcription activity in keratinocyte cells (FIG. 2), whereas in EPCx-treated human monocyte-like cells, the NF-kB levels were comparable to those obtained in the THP-1 cells treated with LPS (FIG. 3).

In Vitro Anti-Tumor Activities

Figure 4:
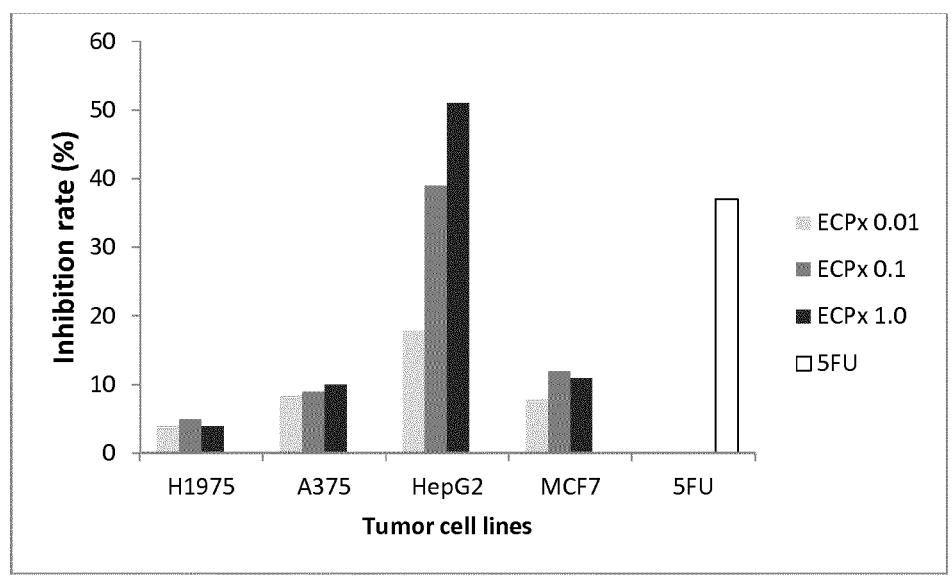
FIG. 4 shows the growth inhibition of EPCx at different concentrations against cancer cell lines in vitro.

The MTT assay was used for measuring the proliferation of the tumor cells. Briefly, human hepatocellular carcinoma cell line (HepG2), human breast adenocarcinoma cell line (MCF7), human lung adenocarcinoma cell line (H1975) and Human melanoma cell line (A375) were seeded at a density of $4 \times 10^4$ cells/mL in a volume of 0.1 mL in 96-well plates, respectively. After 24 h, different concentrations of EPCx (1.0, 0.1 and 0.01 mg/ml) were dissolved in the medium was added to each well and incubated for 48 h at 37° C. in a CO$_2$ incubator. 5-Fu (5-fluorouracil) was used as the positive control. After the incubation, 20 μL of MTT solution (5 mg/mL) were added into each well and followed by further incubation for 4-5 h. The culture media were then removed and 100 μL of DMSO was added to each well for 1 h. Absorbance at 570 nm was detected by microplate ELISA reader. The inhibition ratio of the tumor cells proliferation was determined, the results are shown in FIG. 4.

MTT assay showed that EPCx markedly inhibited proliferation of human hepatocellular carcinoma cell line (HepG2) in a dose-dependent manner (FIG. 4), with little effect on growth of human breast adenocarcinoma cell line (MCF7), human lung adenocarcinoma cell line (H1975) and Human melanoma cell line (A375). The potency of EPCx (at 1.0 mg/mL) to HepG2 cells was found to be similar to 5-fluorouracil (5-FU, IC50 was 10.0 μmol/L).

The foregoing description of preferred embodiments and examples is intended only to acquaint others skilled in the art with Applicants' invention, its principles, and its practical application so that others skilled in the art may adapt and apply the invention in its numerous forms, as they may be best suited to the requirements of a particular use. This detailed description and its specific examples, while indicating preferred embodiments of this invention, are intended for purposes of illustration only. This invention, therefore, is not limited to the preferred embodiments described in this specification, and may be variously modified.

REFERENCES

Bazani Cabral de Melo, F. C., Borsato, D., de Macedo Junior, F. C., Mantovani, M. S., Luiz, R. C., & Pedrine Colabone Celligoi, M. A. (2015). Study of levan productivity from *Bacillus subtilis* Natto by surface response methodology and its antitumor activity against HepG2 cells using metabolomic approach. *Pakistan Journal of Pharmaceutical Sciences*, 28(6), 1917-1926.

Beutler, B. (2004). Innate immunity: an overview. *Molecular Immunology*, 40(12), 845-859.

Ciszek-Lenda, M., Nowak, B., Srottek, M., Gamian, A., & Marcinkiewicz, J. (2011). Immunoregulatory potential of exopolysaccharide from *Lactobacillus rhamnosus* KL37. Effects on the production of inflammatory mediators by mouse macrophages. *International Journal of Experimental Pathology*, 92(6), 382-391.

De Vuyst, L., De Vin, F., Vaningelgem, F., & Degeest, B. (2001). Recent developments in the biosynthesis and applications of heteropolysaccharides from lactic acid bacteria. *International Dairy Journal*, 11(9), 687-707.

Freitas, F., Alves, V. D., & Reis, M. A. M. (2011). Advances in bacterial exopolysaccharides: from production to biotechnological applications. *Trends in Biotechnology*, 29(8), 388-398.

Gamal-Eldeen, A. M., Ahmed, E. F., & Abo-Zeid, M. A. (2009). In vitro cancer chemopreventive properties of polysaccharide extract from the brown alga, *Sargassum latifolium*. *Food and Chemical Toxicology*, 47(6), 1378-1384.

GarclA Sanz, M. N., Ferrer Montiel Antonio, V., Soley Astals, A., & AlmiÑAna DomÉNech, N. (2015). WO Patent No. WO 2015/063240 A1.

Gorska, S., Schwarzer, M., Jachymek, W., Srutkova, D., Brzozowska, E., Kozakova, H., et al. (2014). Distinct Immunomodulation of Bone Marrow-Derived Dendritic Cell Responses to *Lactobacillus plantarum* WCFS1 by Two Different Polysaccharides Isolated from *Lactobacil-* lus rhamnosus LOCK 0900. *Applied and Environmental Microbiology,* 80(20), 6506-6516.

Honda, S., Akao, E., Suzuki, S., Okuda, M., Kakehi, K., & Nakamura, J. (1989). HIGH-PERFORMANCE LIQUID-CHROMATOGRAPHY OF REDUCING CARBOHYDRATES AS STRONGLY ULTRAVIOLET-ABSORBING AND ELECTROCHEMICALLY SENSITIVE 1-PHENYL-3-METHYL-5-PYRAZOLONE DERIVATIVES. *Analytical Biochemistry,* 180(2), 351-357.

Kim, H. S., Hong, J. T., Kim, Y., & Han, S.-B. (2011). Stimulatory Effect of beta-glucans on Immune Cells. *Immune network,* 11(4), 191-195.

Laemmli, U. K. (1970). CLEAVAGE OF STRUCTURAL PROTEINS DURING ASSEMBLY OF HEAD OF BACTERIOPHAGE-T4. *Nature,* 227(5259), 680-&.

Li, J., Qian, W., Xu, Y., Chen, G., Wang, G., Nie, S., et al. (2015). Activation of RAW 264.7 cells by a polysaccharide isolated from Antarctic bacterium Pseudoaltermonas sp S-5. *Carbohydrate Polymers,* 130, 97-103.

Loing, E., Briatte, S., Vayssier, C., Beaulieu, M., & Dionne, P. (2009). WO Patent No. WO 2009/127057 A1.

MercadÉ Gil M$^a$, E., CarriÓN Fonseca, O., & Montes LÓPez M$^a$, J. (2015). WO Patent No. WO 2015/117985 A1.

Miranda, C. C. B. O., Dekker, R. F. H., Serpeloni, J. A., Fonseca, E. A. L., Couls, L. M. S., & Barbosa, A. M. (2008). Anticlastogenic activity exhibited by botryosphaeran, a new exopolysaccharide produced by *Botryosphaeria rhodina* MAMB-05. *International Journal of Biological Macromolecules,* 42(2), 172-177.

Moraine, R. A., & Rogovin, P. (1966). KINETICS OF POLYSACCHARIDE B-1459 FERMENTATION. *Biotechnology and Bioengineering,* 8(4), 511-&.

Nevot, M., Deroncele, V., Lopez-Iglesias, C., Bozal, N., Guinea, J., & Mercade, E. (2006). Ultrastructural analysis of the extracellular matter secreted by the psychrotolerant bacterium *Pseudoalteromonas antarctica* NF3. *Microbial Ecology,* 51(4), 501-507.

Nevot, M., Deroncele, V., Messner, P., Guinea, J., & Mercade, E. (2006). Characterization of outer membrane vesicles released by the psychrotolerant bacterium *Pseudoalteromonas antarctica* NF3. *Environmental Microbiology,* 8(9), 1523-1533.

Nwodo, U. U., Green, E., & Okoh, A. I. (2012). Bacterial Exopolysaccharides: Functionality and Prospects. *International Journal of Molecular Sciences,* 13(11), 14002-14015.

Poli, A., Anzelmo, G., & Nicolaus, B. (2010). Bacterial Exopolysaccharides from Extreme Marine Habitats: Production, Characterization and Biological Activities. *Marine Drugs,* 8(6), 1779-1802.

Quesada, E., Bejar, V., & Calvo, C. (1993). EXOPOLYSACCHARIDE PRODUCTION BY *VOLCANIELLA EURIHALINA. Experientia,* 49(12), 1037-1041.

Raafat, E. M., Gamal-Eldeen, A. M., El-Hussieny, E. A., Ahmed, E. F., & Eissa, A. A. (2014). Polysaccharide extracts of the brown alga *Sargassum asperifolium* possess in vitro cancer chemopreventive properties. *Natural Product Research,* 28(24), 2304-2311.

Rainey, F. A., WardRainey, N., Kroppenstedt, R. M., & Stackebrandt, E. (1996). The genus *Nocardiopsis* represents a phylogenetically coherent taxon and a distinct actinomycete lineage: Proposal of Nocardiopsaceae fam nov. *International Journal of Systematic Bacteriology,* 46(4), 1088-1092.

Rasulov, M. M., Kuznetsov, I. G., Slutskii, L. I., Velikaia, M. V., Zabozlaev, A. G., & Voronkov, M. G. (1993). The ulcerostatic effect of the exopolysaccharide from *Bacillus mucilaginosus* and its possible mechanisms. *Biulleten' eksperimental'noi biologii i meditsiny,* 116(11), 504-505.

Shao, L., Wu, Z., Zhang, H., Chen, W., Ai, L., & Guo, B. (2014). Partial characterization and immunostimulatory activity of exopolysaccharides from *Lactobacillus rhamnosus* KF5. *Carbohydrate Polymers,* 107, 51-56.

Sun, Z., Li, M. J., Qi, Q. S., Gao, C. J., & Lin, C. S. K. (2014). Mixed Food Waste as Renewable Feedstock in Succinic Acid Fermentation. *Applied Biochemistry and Biotechnology,* 174(5), 1822-1833.

Ventosa, A., Garcia, M. T., Kamekura, M., Onishi, H., & Ruizberraquero, F. (1989). BACILLUS-HALOPHILUS SP-NOV, A MODERATELY HALOPHILIC *BACILLUS* SPECIES. *Systematic and Applied Microbiology,* 12(2), 162-166.

Yang, J., Li, X., Xue, Y., Wang, N., & Liu, W. (2014). Anti-hepatoma activity and mechanism of corn silk polysaccharides in H22 tumor-bearing mice. *International Journal of Biological Macromolecules,* 64, 276-280.

Yang, X. B., Zhao, Y., Wang, Q. W., Wang, H. F., & Mei, Q. B. (2005). Analysis of the monosaccharide components in *Angelica* polysaccharides by high performance liquid chromatography. *Analytical Sciences,* 21(10), 1177-1180.

Yang, X. B., Zhao, Y., Zhou, S. Y., Liu, L., Wang, H. F., & Mei, Q. B. (2005). Analysis of monosaccharide composition in *Angelica* polysaccharides by precolumn derivatization high performance liquid chromatography. *Chinese Journal of Analytical Chemistry,* 33(9), 1287-1290.

Yasuda, E., Serata, M., & Sako, T. (2009). Suppressive Effect on Activation of Macrophages by *Lactobacillus casei* Strain Shirota Genes Determining the Synthesis of Cell Wall-Associated Polysaccharides (vol 74, pg 4746, 2008). *Applied and Environmental Microbiology,* 75(4), 1221-1221.

Ye, S., Zhang, J., Liu, Z., Zhang, Y., Li, J., & Li, Y. O. (2016). Biosynthesis of selenium rich exopolysaccharide (Se-EPS) by *Pseudomonas* PT-8 and characterization of its antioxidant activities. *Carbohydrate Polymers,* 142, 230-239.

Zhang, F., Liu, Y. E., Wang, W., Zhao, Y. U., & Li, Z. (2015). CN Patent No. CN 104694594 A.

Zheng, Y., Wang, W.-d., & Li, Y. (2015). Antitumor and immunomodulatory activity of polysaccharide isolated from *Trametes orientalis. Carbohydrate Polymers,* 131, 248-254.

The invention claimed is:

1. A method of inhibiting proliferation of human hepatocellular carcinoma cells in a subject in need thereof, comprising administering a dose of a composition comprising an exopolysaccharide-protein complex obtained from a bacterium of the genus *Halomonas* comprising:
   (i) a crude exopolysaccharide, and
   (ii) exopolysaccharide-associated proteins which are derived from outer membrane vesicles and have a molecular weight between 30 and 250 kDa, wherein the exopolysaccharide-associated proteins include two bands of molecular weight corresponding to a band between 30 kDa and 40 kDa and a band between 51 kDa and 60 kDa as obtained by SDS-PAGE,
   wherein the exopolysaccharide-protein complex has a concentration in the composition of 0.01 mg/ml to 1.0 mg/ml.

2. The method according to claim 1, wherein the exopolysaccharide-protein complex comprises a crude exopolysaccharide heteropolymer comprising glucose, galactose, uronic acid units, and other sugar units selected from rhamnose, glucosamine, and a mixture of rhamnose and glucosamine.

3. The method according to claim 2, wherein the crude exopolysaccharide heteropolymer comprises: 30 to 60 wt % glucose, 30 to 50 wt % galactose, 5 to 10 wt % uronic acids, and 1 to 10% of other sugar units, provided that the sum of the components in the crude exopolysaccharide is 100 wt %.

4. The method according to claim 2, wherein the crude exopolysaccharide heteropolymer further comprises sulfate at a concentration from 2 to 10 wt %.

5. The method according to claim 1, the composition further comprising a biological response modifier selected from the group consisting of a lymphokine, an interleukin, a growth factor, and an NFkB factor.

6. The method according to claim 1, wherein the composition is a pharmaceutical, nutraceutical or cosmeceutical composition.

7. The method according to claim 1, further comprising stimulating an immune response in a subject.

8. The method according to claim 7, wherein the disease associated with an undesirable inflammatory activity is selected from an allergy, Alzheimer's disease, arthritis, autoimmune deficiency syndrome, celiac disease, diabetes mellitus, a gastrointestinal disorder, inflammatory bowel disease, interstitial cystitis, a skin disorder, acne, arteritis, arthritis, cancer, cellulitis, dermatitis, and a cardiovascular disease.

9. The method according to claim 7, wherein the cancer is a liver cancer or a hepatocellular carcinoma.

10. The method according to claim 1, wherein the exopolysaccharide-protein complex is an anticancer agent or an adjuvant agent for a cancer therapy.

11. The method according to claim 1, wherein the composition inhibits proliferation of human hepatocellular carcinoma cells in a dose dependent manner.

* * * * *